United States Patent [19]

Simon

[11] Patent Number: 5,741,297
[45] Date of Patent: Apr. 21, 1998

[54] DAISY OCCLUDER AND METHOD FOR SEPTAL DEFECT REPAIR

[76] Inventor: Morris Simon, 8 Otis Pl., Boston, Mass. 02108

[21] Appl. No.: 697,832

[22] Filed: Aug. 28, 1996

[51] Int. Cl.⁶ .................................................. A61B 17/08
[52] U.S. Cl. ........................... 606/213; 606/215; 606/151; 604/285
[58] Field of Search .................................. 606/213, 215, 606/151; 600/32; 623/11; 604/285, 286

[56] References Cited

U.S. PATENT DOCUMENTS

| | | |
|---|---|---|
| 3,874,388 | 4/1975 | King et al. . |
| 4,007,743 | 2/1977 | Blake . |
| 4,917,089 | 4/1990 | Sideris . |
| 5,108,420 | 4/1992 | Marks . |
| 5,192,301 | 3/1993 | Kamiya et al. . |
| 5,254,133 | 10/1993 | Seid ........................................ 606/215 |
| 5,284,488 | 2/1994 | Sideris . |
| 5,334,217 | 8/1994 | Das . |
| 5,350,399 | 9/1994 | Erlebacher et al. ................ 606/213 |
| 5,366,478 | 11/1994 | Brinkerhoff et al. . |
| 5,425,744 | 6/1995 | Fagan et al. . |
| 5,451,235 | 9/1995 | Lock et al. . |
| 5,486,193 | 1/1996 | Bourne et al. . |

FOREIGN PATENT DOCUMENTS

| | | |
|---|---|---|
| 2822603 | 11/1979 | Germany . |
| 3116462 | 12/1982 | Germany . |
| 9601599 | 1/1996 | WIPO . |

OTHER PUBLICATIONS

*Double–Umbrella Closure of Atrial Defects*, "Initial Clinial Applications" by Jonathan J. Rome, MD, John F. Keane, MD, Stanton B. Perry, MD, Philip J. Spevak, MD, and James E. Lock, MD, (date unknown).

*Transcatheter Closure of Atrial Septal Defects*, "Experimental Studies" by James E. Lock, MD, Joanthan J. Rome, MD, Rudy Davis, BS, MBA, Stella Van Praagh, MD, Stanton B. Perry, MD, Richard Van Praagh, MD and John F. Keane, MD, Circulation, vol. 79, No. 5, May 1989, pp. 1091–1099.

Primary Examiner—Michael Buiz
Assistant Examiner—Tina T. D. Pham
Attorney, Agent, or Firm—Sixbey, Friedman, Leedom & Ferguson PC; Daniel W. Sixbey

[57] ABSTRACT

The star occluder includes a frame formed from a first plurality of arms extending radially in a first plane and a second plurality of arms extending radially in a second plane which is spaced from and substantially parallel to the first plane. Loop joinder legs extend between the base ends of the first and second arms, and a first membrane sheet is supported by and extends over the first plurality of arms while a second membrane sheet is supported by and extends over the second group of arms. The frame is somewhat flexible when expanded so that the loop joinder legs expand into contact with the periphery of a septal defect and determine the size to which the frame will expand.

29 Claims, 5 Drawing Sheets

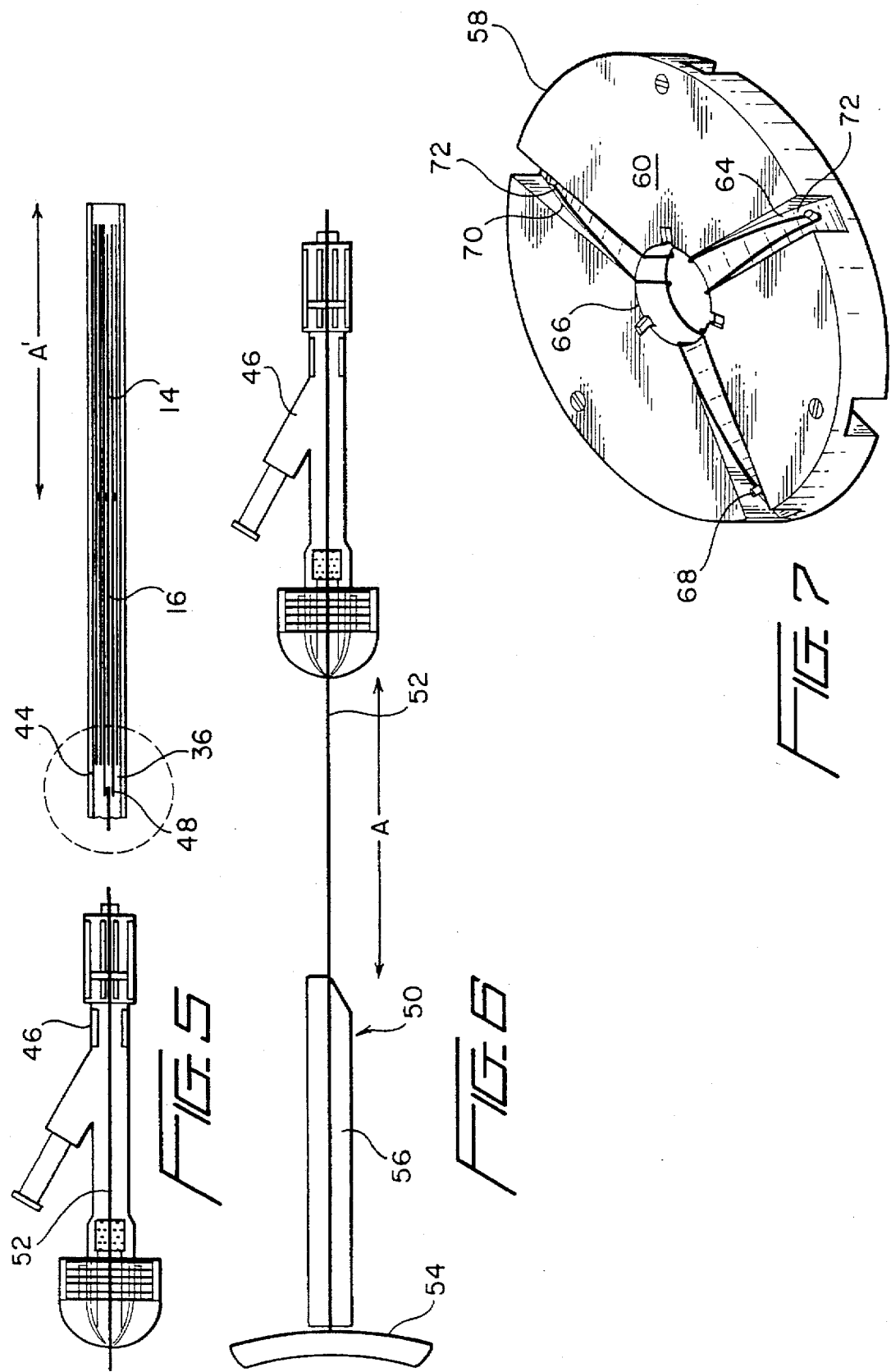

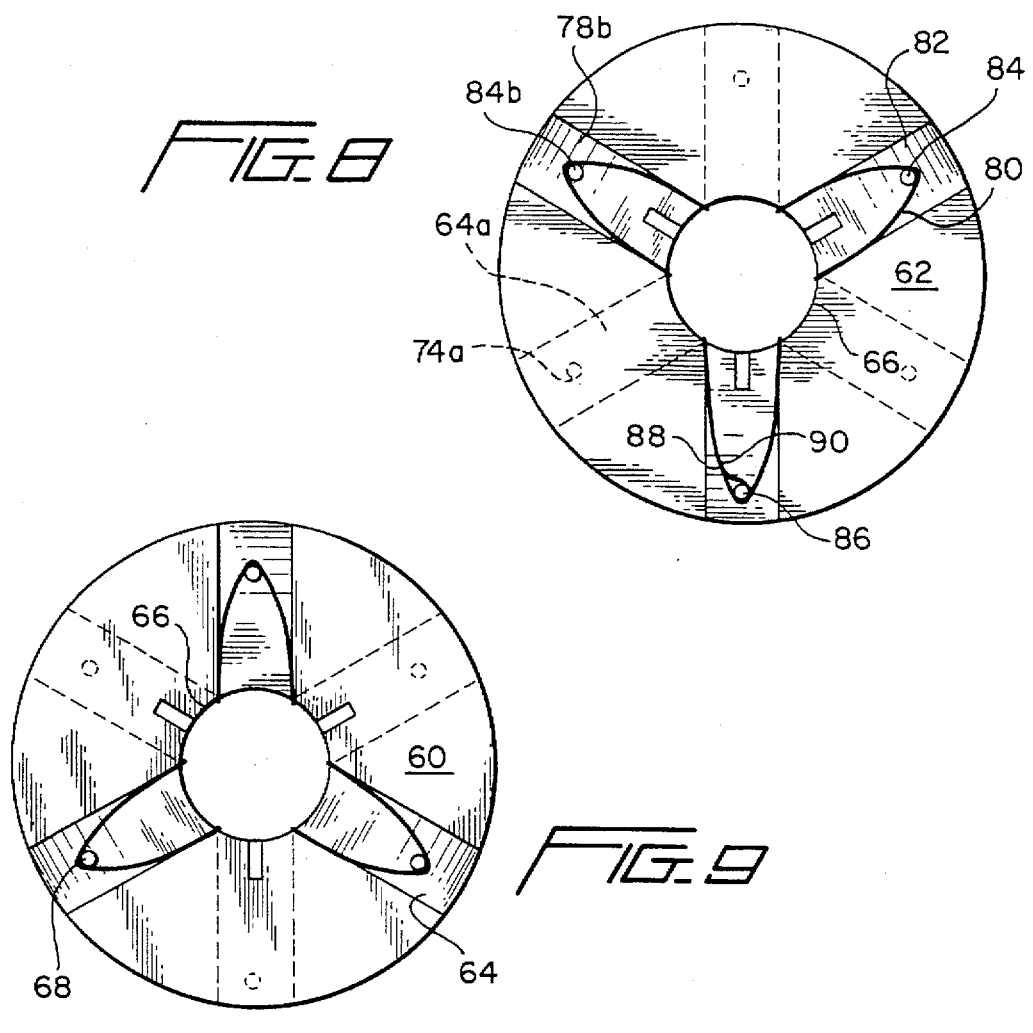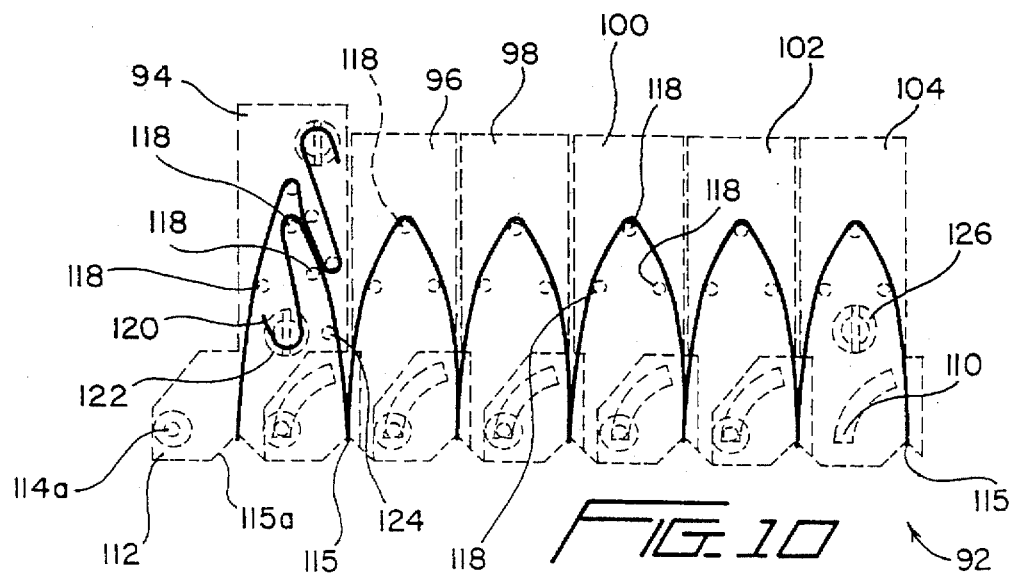

5,741,297

DAISY OCCLUDER AND METHOD FOR SEPTAL DEFECT REPAIR

FIELD OF THE INVENTION

The present invention relates to an occluder structure and method for the repair of intracardiac and vascular septal defects, as well as other abnormal openings in tissue planes such as the abdominal wall.

BACKGROUND OF THE INVENTION

A septum, which is a thin wall of muscle or tissue which divides two or more chambers of the heart or other anatomic spaces of the human body, sometimes is perforated by an abnormal aperture passing through the septum, described as a septal defect. When septal defects occur between adjacent chambers of the heart or its associated major blood vessels, blood can leak from one chamber or artery to another imposing added strain on the heart which may lead to heart failure. An opening in the abdominal wall may allow bowel to pass through it, causing a hernia.

The surgical repair of intracardiac defects has required the use of open chest surgical techniques wherein the defect is directly sutured shut. Consequently, a number of devices have been developed to close clinically significant defects without surgery. For example, U.S. Pat. No. 3,874,388 to King et al. and U.S. Pat. No. 4,007,743 to Blake both disclose umbrella-like occluders which are positioned across a septal defect to accomplish closure.

Dr. William Rashkind developed an umbrella type occluder which relied upon hooks to attach the device on one side of the atrial septum. This device was difficult to position and the hooks were very difficult to disengage.

U.S. Pat. No. 4,917,089 to Sideris discloses an occluder which is positioned on the distal side of a defect and an occluder holder which is positioned on the proximal side. These elements are separately delivered to the site of the defect and then connected together by a button closure. The extensive manipulation required to connect and deploy this device increases the likelihood that the device will be improperly positioned or accidentally released into the bloodstream.

Fagan et al. U.S. Pat. No. 5,425,744 discloses a dual umbrella-type occluder which may be deployed as a single unitary unit, while U.S. Pat. No. 5,451,235 to Lock et al. shows a similar occlusion device wherein the dual umbrella units are interconnected to allow relative movement so as to provide improved seating of the device. Proper positioning and seating of an occluder has been a problem which was difficult to solve with previously known devices, and a need exists for a septal occluder which is self centering, self locating, and which effectively closes septal defects in a range of sizes and shapes.

SUMMARY OF THE INVENTION

It is a primary object of the present invention to provide a novel and improved septal defect occluder which is self centering, self locating and which effectively closes septal defects within a range of sizes and shapes.

Another object of the present invention is to provide a novel and improved septal defect occluder including a wire frame formed of a single length of wire with only a single weld. The frame is preferably formed with triple front and rear petal loops extending in overlapping planes, though quadruple, quintuple or more loops could be used on both sides.

Still another object of the present invention is to provide a novel and improved septal defect occluder formed with front and rear alternative petal loops extending in spaced, substantially parallel planes which are joined at the loop inner ends by loop joinder links which extend between alternate front and rear petals and the overlapping planes of the petal tips. The loop joinder links extend through the opening in the septum so that the deployed device will expand and adjust automatically to fit the size and shape of the opening.

Yet another object of the present invention is to provide a novel and improved septal defect occluder having a frame with joined front and rear petal loops extending in spaced, substantially parallel planes with soft, stretchable sheets of polymer material extending over the front and rear sets of loops and which are held in place without stitching. The sheets of material are formed with pockets which receive the tips of the petal loops of the occluder frame.

A further object of the present invention is to provide a novel and improved method and mandrel for forming a septal occluder frame from a single length of spring wire or shape memory material wherein the frame includes joined occluder petal loops extending in overlapping, substantially parallel planes.

Yet a further object of the present invention is to provide a novel and improved delivery unit and method for delivering and locating a septal defect occluder.

Another object of the present invention is to provide a novel and improved septal defect occluder having a frame formed from radially extending looped petals where all loops are resilient enough to move independently when the frame is expanded. The loops are joined by joinder links at the center of the frame with sufficient flexibility to expand to fit a defect in the septum as it enlarges over time.

A still further object of the invention is to provide a novel and improved septal defect occluder having a frame formed from radially extending looped petals which are joined by joinder links at the center of the frame. A removable lasso looped about the joinder links aids in delivering and positioning the occluder and can be used to contract and retrieve an improperly positioned occluder.

BRIEF DESCRIPTION OF THE DRAWINGS

FIG. 5 is a sectional view of the distal and proximal ends of a delivery catheter system for the septal defect occluder of the present invention;

FIG. 6 is a sectional view of the pusher handle of the delivery unit of FIG. 5;

FIG. 7 is a perspective view of a jig for forming the frame for the occluder of the present invention;

FIG. 8 is a plan view of one side of the jig of FIG. 7;

FIG. 9 is a plan view of the opposite side of the jig of FIG. 8;

FIG. 10 is a plan view of a second embodiment of a jig for forming the occluder of the present invention with the plates in a straight-line configuration;

3

Figure 11:
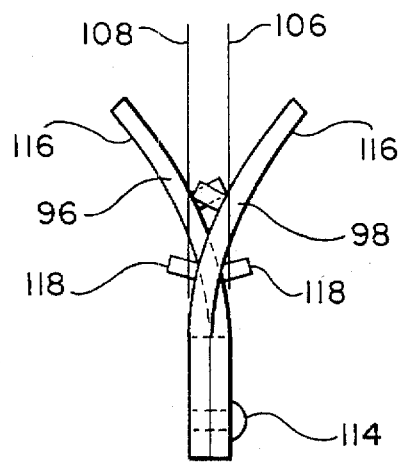
Figure 12:
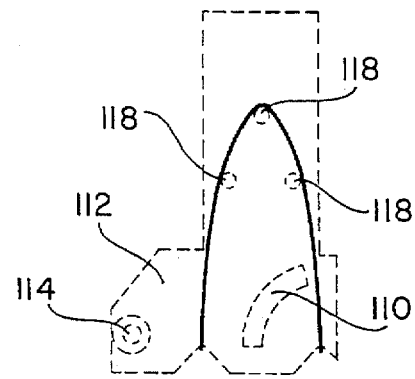
Figure 13:
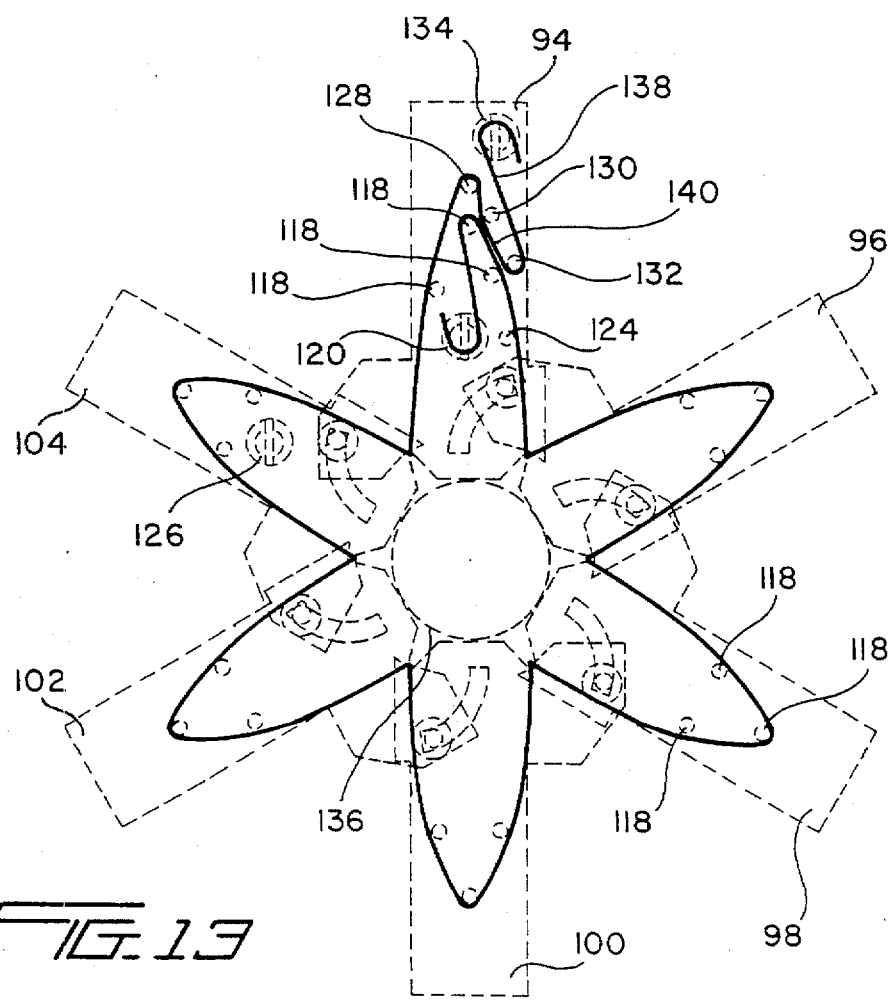
Figure 14:
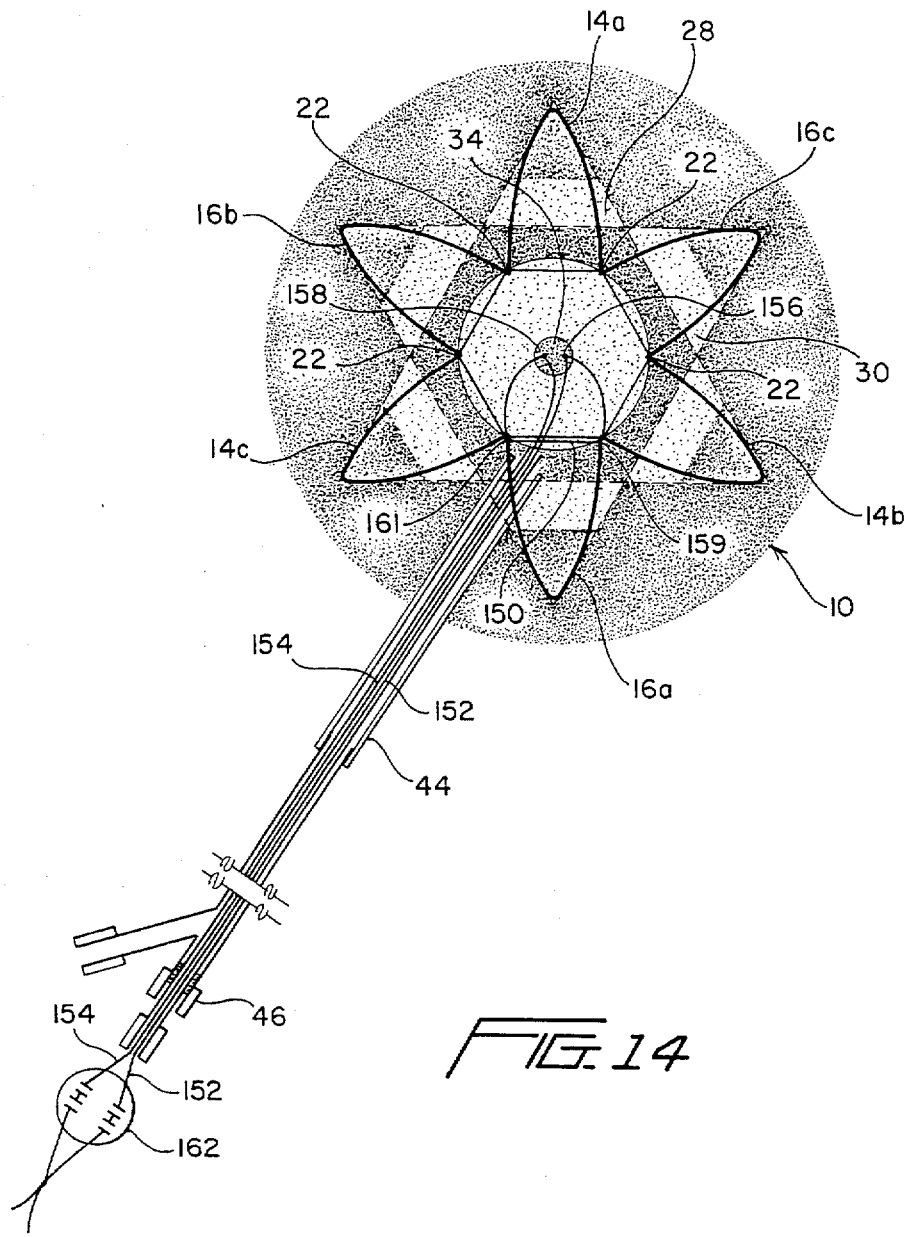

FIG. 11 is a view in side elevation of two adjacent plates for the jig of FIG. 10;

FIG. 12 is a plan view of a single plate for the jig of FIG. 10;

FIG. 13 is a plan view of the jig of FIG. 10 with the plates in a circular configuration; and FIG. 14 is a diagrammatic plan view of an expanded occluder of the present invention showing the positioning lasso construction and a sectional view of a delivery unit.

DESCRIPTION OF THE PREFERRED EMBODIMENTS

Referring now to the drawings, the daisy septal defect occluder of the present invention indicated generally at 10 includes a wire frame 12 preferably formed from a single length of wire. The frame 12 includes a front set of spaced, loop shaped petals 14 including petals 14a, 14b and 14c extending outwardly in a first plane and a rear set of loop shaped petals including petals or arms 16a, 16b and 16c extending outwardly in a second plane spaced from, and substantially parallel to, said first plane. It will be noted that each of the rear loop shaped petals is positioned between two of the front loop shaped petals and is connected at its two base points 18 to base points 20 of the two adjacent front loop shaped petals by loop joinder links 22. These loop joinder legs are arranged around the circumference of a circle which will expand or contract depending upon the size of the defect in a septum 23 through which the joinder links will extend when the occluder is in place.

Figure 1:
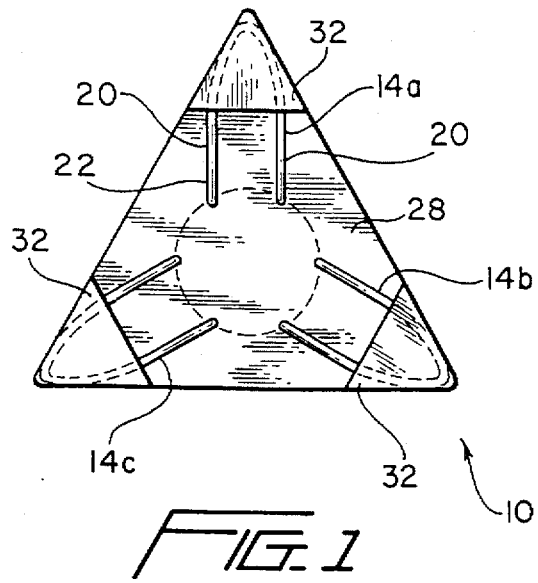
FIG. 1 is a plan view of one side of the septal defect occluder of the present invention.
Figure 2:
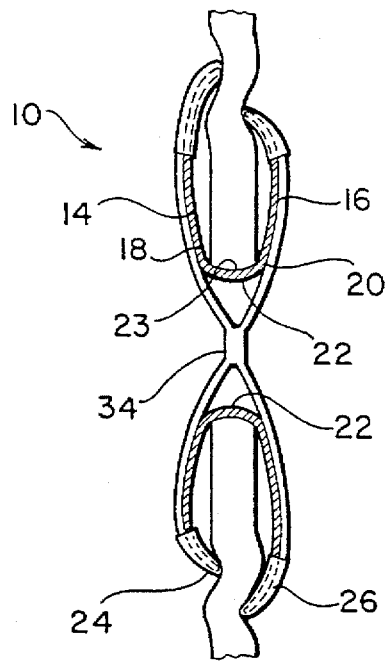
FIG. 2 is a sectional view of a fully deployed occluder of the present invention.
Figure 3:
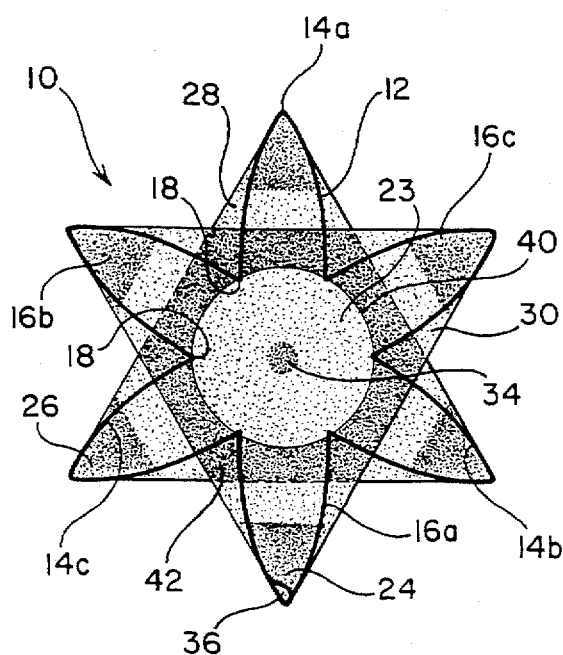
FIG. 3 is a diagrammatic plan view of a deployed occluder of the present invention in a large defect.
Figure 4:
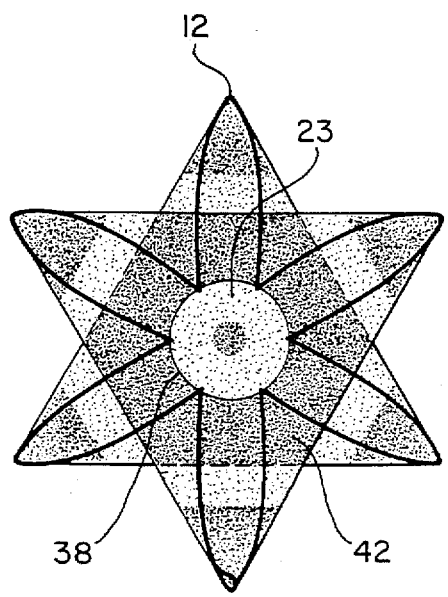
FIG. 4 is a diagrammatic plan view of a similar deployed occluder of the present invention in a small defect.

The wire frame 12 is formed of a length of resilient wire which may be a spring metal wire, but which preferably is formed of a shape memory material such as nitinol. By forming the frame of an alloy material, such as nitinol, transition between the martensitic and austenitic states of the material can be achieved by temperature transitions above and below a transition temperature or transition temperature range. Such controlled temperature transitions are employed to render the frame flexible so that it can be compacted to facilitate passage through a thin catheter (FIG. 5) and to subsequently expand and rigidify the frame within and over a septal defect. In the expanded state, the frame rigidities to an extent necessary to maintain is expanded shape but is flexible enough to expand or contract within a range to accommodate a range of septal opening sizes and shapes. This is true of both frames formed of spring wire or shape memory material. The longest and smallest expansion points for one size of frame are illustrated by FIGS. 3 and 4, respectively. Frames can be formed to fit a number of size ranges.

When the wire frame 12 is in the expanded state, the tips 24 of the rear petals 16a, 16b and 16c are curved forwardly toward the front petals and the tips 26 of the front petals 14a, 14b and 14c are curved rearwardly toward the rear petals so that the planes of the alternating petal tips may overlap. When the occluder 10 is positioned over a septal defect, these petal tips engage and corrugate the septum 23 to hold the occluder in place.

The front petals 14a, 14b and 14c of the frame 12 support a polygonal membrane or sheet of material 28 while the rear petals 16a, 16b and 16c support a polygonal membrane or sheet of material 30. These sheets, which are triangular when three petals 14 and 16 are used, form spaced closure units for a septal defect to span and close the proximal and distal sides of the defect, and are formed of a material having some elasticity such as sheets of elastic dacron. Each triangular sheet is similar in construction and is formed with a pocket

4

32 at each point of the triangle to receive the end tips of either the front or rear petals. Thus the front petals support the front sheet 28 and the rear petals support the back sheet 30 without having the front and rear sheets stitched to the wire frame 12.

To maintain the petals of the frame 12 in place within the pockets 32 of the front and back sheets, these sheets are bonded together centrally at 34, and the pockets 32 are made deep enough to retain the petals throughout the expansion range of the wire frame 12. In one embodiment, one rear petal 16a is formed to be longer than the remaining front and rear petals, and the pocket 32 which retains this petal is provided with an opening at the apex thereof to permit the loop end 36 of this petal to be exposed. This loop end passes through the opening and provides a recess to receive a hook member for positioning the occluder 10.

As will be noted from FIGS. 3 and 4, a single occluder 10 will effectively close septal defects within a range from a small defect opening 38 to a large defect opening 40. This is caused by the fact that the loop joinder links 22 which pass through the opening in the septum permit the frame 12 to expand until the loop joinder links engage the edges of the opening in the septum. This not only adjusts the frame so that the occluder closes openings of various sizes, but it also automatically centers the occluder over the defect opening. This is extremely important, as with previously known occluders, proper positioning of the occluder relative to the defect opening has been difficult to achieve. It will be noted that the six sided hexagonal area of overlap between the front sheet 28 and back sheet 30, indicated by the darkened area 42, is greater than the area of the defect openings 38 and 40, so that the occluder 10 very effectively closes any opening within its range of operation. The loop shaped petals 14 and 16, when the occluder 10 is expanded, define a circle with arms extending at sixty degree angles around the circle. The petals extending in one plane define the points of a triangle, and the petals of both planes support two offset triangular sheets where the points at the triangles are offset by sixty degrees.

FIGS. 5 and 6 disclose a simple delivery device for the occluder 10. The occluder is compressed within an open ended tubular portion 44 of a catheter delivery system 46 with the front petals 14 positioned toward the forward or distal open end of the tubular portion and the rear petals 16 pointing backward toward the proximal end. The loop end 36 of the petal 16a projects rearwardly for engagement with a hook 48 at the end of a delivery unit 50. The delivery unit includes an elongate wire 52 with the hook 48 formed at the distal end thereof and a handle 54 formed at the proximal end. The wire 52 extends through the catheter 46 to bring the hook 48 into engagement with the loop end 36. With the hook engaged, a sleeve 56 pivoted to the handle 54 is pivoted downwardly into engagement with the wire 52, to define a distance A between the sleeve and catheter equal to the distance A' required to deploy the front petals 14 from the open end of the catheter tube 44. Once the catheter is positioned with the distal end of the catheter tube 44 through the opening in the septum, the handle 54 is moved forwardly until the sleeve 56 engages the catheter to deploy the front petals 14 on the distal side of the septum. Then the sleeve is pivoted upwardly, and the catheter is withdrawn to deploy the rear petals 16. The hook is now disengaged from the extruded loop end 36 and the entire delivery unit is withdrawn.

A safety monofilament lasso tether may be used when the occluder device is deployed so that it can be retrieved in an emergency if the deployed device is improperly seated over the septal defect. The monofilament loop extends the entire length of the delivery system and is positioned around the central links between the front and rear petals. If the device is correctly seated, the monofilament lasso is simply withdrawn after releasing one end. The entire delivery system is then removed. If the device is improperly seated, the tip of the delivery catheter is advanced so that the lasso is tightened and the device can be forcibly pulled into the catheter or a larger sheath and removed entirely.

A first mandrel or jig 58 for forming the wire frame 12 is illustrated in FIGS. 7, 8 and 9. This jig is formed of metal and is disc shaped in configuration with a top surface 60 and a bottom surface 62. The top surface of the jig is provided with three grooves 64 which extend radially outward at 120° angles from the circumference of a hole 66 in the center of the jig. The bottom surface 70 at the outermost extremity of each groove 64 curves downwardly at 72 toward the bottom surface 62 of the jig for the purpose of curving the tip areas 26 of the petals 14a, 14b and 14c. Pins 68 are mounted to project upwardly from the bottom surface of each groove 64 at the outermost extremity thereof, and these pins are equally spaced from the circle 66.

The base points 20 of the front petals 14 are defined by the circular hole 66 at the innermost extremity of each of the two sidewalls of each groove 64. The hole 66 extends through the jig between the top and the bottom surfaces thereof.

The bottom surface of the jig 58 is provided with three radially extending grooves 78 which extend outwardly at 120° angles from the circle 66. Each groove 78 is positioned midway between two grooves 64, and it will be noted that the width of the grooves 64 and 78 is such that the grooves converge at the central hole 66. Like the grooves 64, the bottom wall 80 of each of the grooves 78 curves at 82 at the outermost extremity of the groove, and in this instance, the curve is toward the top surface 60. Pins 84 project upwardly from the bottom wall 80 of two of the grooves 78, and these pins are spaced from the circle 66 for a distance equal to that of the pins 74. However, a third pin 86 in the remaining groove 78 projects upwardly from the bottom wall 80 of that groove and is spaced from the circle 66 for a distance which is greater than that of the remaining pins 74 and 84.

To form the wire frame 12, a single length of wire having a first end 88 is hooked around the pin 86 and is then fed up through a hole 66 and down groove 64a and around pin 68 and then back through hole 66 to pin 84b in groove 78b. This alternative winding action continues around the jig 58 until the wire passes through the hole 66 and around the pin 86 where it meets the first wire end 88 at 90 and both ends are held by a locking screw. After annealing the two ends are welded together. Thus the wire frame 12 is formed from a single wire with a single weld, and the added length of the petal formed about the pin 86 provides the loop end 36 in this petal. The bottom surfaces 70 of the grooves 64 are spaced from the bottom surfaces 80 of the grooves 78 so that the wire petals formed in the grooves 64 extend outwardly in a plane which is substantially parallel to, but spaced from, a plane in which the wire petals formed in the grooves 78 extend.

When the frame 12 is formed of nitinol wire, the jig 58 is placed in an oven once the wire is wound in place to anneal the wire and set the final expanded shape of the device. Then the finished frame 12 is removed from the jig and the single wire weld is completed.

An alternative star jig 92 for forming the frame 12 is illustrated in FIGS. 10, 11, 12 and 13. The star jig includes six pivotally connected elongated metal plates 94, 96, 98, 100, 102 and 104. The plates 94, 98 and 102 provide petals which extend in a first plane 106 while the plates 96, 100 and 104 are used to form petals which extend in a second substantially parallel, spaced plane 108. Each plate includes a curved guide slot 110 in the base area thereof and a laterally projecting lug 112 adjacent to the guide slot which supports an upwardly projecting point pin 114. The pivot pin is positioned to extend through the lowermost end of the guide slot in the next adjacent plate, and the pivot pins for the plates 96–104 are fixed while the pivot pin 114a for the plate 94 is removable. At the lowermost extremity of each plate on the side opposite to the lug 112 is an outwardly projecting notch 115. This notch is aligned with a notch 115a in the lug.

To create petals for the wire frame 12 with inwardly curving tips 24 and 26, the outer extremities of the plates 94, 98 and 102 are curved at 116 toward and overlap the plates 96, 100 and 104, while the outer extremities of these remaining plates at 116 curve toward and overlap the plates 94, 98 and 102. Each plate, at the outer extremity 116, includes three outwardly projecting spaced pins 118 which are used to form the front petals 14 and rear petals 16 of the wire frame 12. It will be noted from FIG. 11, that the pins 118 on the plates 94, 98 and 102 are formed on the outermost surface of these plates opposite to the outermost surface of the plates 96, 100 and 104 which bears the pins 118. Thus the pins 118 on the plates 96, 100 and 104 extend in a direction opposite to that of the pins 118 on the plates 94, 98 and 102.

To wind a single length of wire on the jig 92, the plates of the jig are positioned in side by side relationship as shown in FIG. 10, and a first end 120 of the wire is locked under a screw 122 on the plate 94. The wire is then wound around two of the three pins 118 on the plate 94 and a fourth pin 124 projecting from the same surface of this plate and then through the notches 115 and 115a to the opposite surface of the plate 96. The wire is then wound around the pins 118 on the plate 96 and then back through the notches 115 and 115a to the pins on the opposite surface of the plate 98. This alternate winding operation continues until the wire has been wound around the pins 118 on the plate 104, at which time the plates are pivoted apart until the curved guide slot 110 on the plate 104 is aligned with a receiving aperture for the removable pivot pin 114a for the plate 94. This pivot pin is now inserted through the slot in the plate 104 and into the lug 112 for the plate 94, and the jig 92 is now locked in the configuration of FIG. 13. The wire is now tightened and held by a temporary holding screw 126 on the plate 104.

The remaining free end of the wire which extends beyond the temporary holding screw 126 is passed through the notch 115 on the plate 104 and the notch 115a on the lug 112 for the plate 94 and then around a pin 118 and additional pins 128, 130 and 132 to a holding screw 134. It will be noted from FIG. 13, that all of the pins 118 are equal distant from a circle 136 shown in broken lines which is defined by the innermost ends of the extended plates 94–104, but that the pin 128 is positioned at a greater distance from the circle to from the loop end 36. The pins 128, 130 and 132 position a second end 138 of the wire adjacent to the first end 120 of the wire, and these wire ends are welded together at 140. Then the jig 92 bearing the wire is placed in an oven to anneal the deployed shape of the device when the wire is formed of nitinol or similar shape memory material when the transition temperature is reached. When the screws 122, 126 and 134 are released, the wire frame 12 can be removed and trimmed around the weld 140.

Once the wire frame 12 is formed and welded, the petals 14 and 16 are inserted into the pockets 32 of the front and back sheets 28 and 30 and the front and back sheets are fused at their center or otherwise attached at 34 of the circularly arranged loop joined links 22.

The loop shaped petals 14 and 16 of the frame 12 are each relatively movable when the frame is expanded so that stresses are not confined to specific areas of the frame. The loop joinder links 22 form a post for the frame at the center thereof, and within the range of expansion of the frame, control expansion in relation to the size of the septal defect which is occluded. In children, as the child and the defect grow in size, the occluder frame adjusts to insure that defect remains covered.

Referring now to FIG. 14, the monofilament lasso tether previously discussed is illustrated. The elongate monofilament tether 150 has two ends 152 and 154 which pass through the catheter delivery system 46.

Beginning at end 152, the tether passes through a first opening 156 in the fused center of the front and rear membrane sheets 28 and 30 and then loops downwardly to reenter a first opening 159 in the front sheet 28 so as to lie in the space between the sheets 28 and 30 and around the loop joinder links 22 between all of the petals 14 and 16. The tether then passes out through a second opening 161 in the front sheet 28 and then loops upwardly through a second opening 158 in the fused center of the rear membrane sheet and back as end 154 through the catheter delivery system. If the occluder 10 is delivered from the catheter delivery system and expanded and seated in the proper position over a defect, one of the tether ends 152 or 154 is cut and a button 162 is pulled to remove the tether from the occluder out through the catheter delivery system. If the occluder is improperly seated over the defect, both ends 152 and 154 of the tether may be pulled back into the catheter delivery system by means of the button 162 causing the tether lasso to tighten around the loop joinder links 22 to cause the occluder to contract toward the center and permit the occluder to be drawn back into the tubular portion 44 of the delivery system. Thus an improperly positioned occluder can easily be withdrawn and later a more appropriately sized occluder device can be inserted and repositioned properly.

I claim:

1. A septal defect occluder comprising:
   a frame adapted to be inwardly radially collapsed from an expanded configuration to a collapsed configuration, said frame in the expanded configuration including a first plurality of spaced, loop shaped arms extending radially in a first plane, said first arms each having a base end formed by two spaced end portions,
   a second plurality of spaced, loop shaped arms extending radially in a second plane substantially parallel to and spaced from said first plane, said second arms each having a base end formed by two spaced end portions,
   and a plurality of spaced loop joinder links extending between the base ends of said first and second arms, an end portion of each of said first arms being connected by one of said plurality of loop joinder links to an end portion of a second arm,
   a first sheet of material supported by and extending over said first arms, and
   a second sheet of material supported by and extending over said second arms.

2. The septal defect occluder of claim 1 wherein said frame is formed from a single elongated strand of material.

3. The septal defect occluder of claim 2 wherein said elongated strand of material is a shape memory material having a first low temperature condition in which said material is relatively pliable and a second high temperature condition wherein said material is resiliently deformable but relatively rigid and wherein said material assumes a predetermined functional form.

4. The septal defect occluder of claim 1 wherein with said frame in the expanded configuration, said base ends of said first and second plurality of arms are configured to define a single central open area, said first and second plurality of arms extending radially outward from the periphery of said central open area and being connected by said loop joinder links at the periphery of said central open area.

5. The septal defect occluder of claim 4 wherein said first and second sheets of material are joined together within said central open area.

6. The septal defect occluder of claim 1 wherein said first plurality arms each have an outermost end section spaced from said base section thereof and said second arms each have an outermost end section spaced from said base section thereof, the outermost end sections of said first arms being curved toward said second arms and the outermost end sections of said second arms being curved toward said first arms when said frame is in the expanded configuration.

7. The septal defect occluder of claim 1 wherein each of said second plurality of spaced arms extends outwardly and centrally between two adjacent arms of said first plurality of spaced arms when said frame is in the expanded configuration.

8. The septal defect occluder of claim 7 wherein said first and second plurality of spaced arms each include at least three arms.

9. The septal defect occluder of claim 7 wherein with said frame in the expanded configuration, each of said first and second plurality of spaced arms is petal shaped in configuration to form petal loops, the base end of each such petal loop being formed by the two spaced end portions, each of which is connected to a loop joinder link extending to an end portion of a petal loop shaped arm in a different plane, each such petal loop being defined by an elongate strand extending radially outward from one of said two spaced end portions and curving to form an arcuate outermost end of petal loop and then extending inwardly to said remaining end portion.

10. The septal defect occluder of claim 9 wherein all but one of said petal shaped arms of both said first and second plurality of arms are of substantially equal length, said one arm being of greater length.

11. The septal defect occluder of claim 9 wherein said frame is formed from a single elongate strand of wire.

12. The septal defect occluder of claim 11 wherein said elongated strand of wire has a first end section and a second end section joined by a weld to form said frame.

13. The septal defect occluder of claim 12 wherein said first plurality of arms each has an outermost end section adjacent to the arcuate outermost end thereof and said second plurality of arms each has an outermost end section adjacent to the arcuate outermost end thereof, the outermost end sections of said first arms being curved toward said second arms and the outermost end sections of said second arms being curved toward said first arms when said frame is in the expanded configuration.

14. The septal defect occluder of claim 13 wherein said first sheet of material is provided with pockets to receive the outermost end sections of said first arms and said second sheet of material is provided with pockets to receive the outermost end sections of said second arms.

15. The septal defect occluder of claim 14 wherein with said frame in the expanded configuration, said base ends of said first and second plurality of arms are configured to define a single central circular area, said first and second plurality arms extending radially outward from said central circular area.

16. The septal defect occluder of claim 15 wherein said first and second sheets of material are joined together within said central circular area.

17. The septal defect occluder of claim 16 wherein said first and second plurality of spaced arms each include three arms.

18. The septal defect occluder of claim 17 wherein said first and second sheets of material are triangular in shape with an apex area at each of the three points of the triangle, said pockets being formed in said apex areas.

19. The septal defect occluder of claim 18 wherein said single elongated strand of wire forming said frame is a shape memory material having a first low temperature condition in which said material is relatively pliable and a second high temperature condition wherein said material is resiliently deformable but relatively rigid and wherein said material assumes a predetermined functional form.

20. The septal defect occluder of claim 19 wherein said first and second sheets of material are formed from elastic dacron.

21. The septal defect occluder of claim 1 which includes an elongate flexible tether having a first end section and a second end section, said first sheet of material having first and second spaced openings positioned centrally thereof, said elongate tether extending from said first end section through said first opening in said first sheet of material and between said first and second sheets of material around said loop joinder links and out through said second opening in said first sheet of material to said second end section.

22. A septal defect occluder comprising:

a frame adapted to be inwardly radially collapsed from an expanded configuration to a collapsed configuration, said frame in the expanded configuration including a first plurality of spaced arms extending radially in a first plane, each of said first arms having a base end and an outermost end section spaced from said base end, a second plurality of spaced arms extending radially in a second plane substantially parallel to and spaced from said first plane, each of said second arms having a base end and an outermost end section spaced from said base end, the outermost end sections of said first arms being curved toward said second arms and the outermost end sections of said second arms being curved toward said arms when said frame is in the expanded configuration, and loop joinder links extending between the base ends of said first and second arms, a first sheet of material supported by and extending over said first arms, and a second sheet of material supported by and extending over said second arms, said first sheet of material being provided with pockets to receive the outermost end sections of said first arms and said second sheet of material being provided with pockets to receive the outermost end sections of said second arms.

23. The septal defect occluder of claim 22 wherein said first and second sheets of material are polygonal in shape with an apex area at each of the points of the polygon, said first sheet of material being supported by one of said first plurality of arms extending into each apex area thereof and said second sheet of material being supported by one of said second plurality of arms extending into each apex area thereof.

24. The septal defect occluder of claim 23 wherein with said frame in the expanded configuration, said base ends of said first and second plurality of arms are configured to define a single central circular area, said first and second plurality arms extending radially outward from said central circular area.

25. The septal defect occluder of claim 24 wherein said first and second sheets of material are joined together within said central circular area.

26. The septal defect occluder of claim 25 wherein said frame is formed from a single elongated strand of material.

27. The septal defect occluder of claim 26 wherein said elongated strand of material is a shape memory material having a first low temperature condition in which said material is relatively pliable and a second high temperature condition wherein said material is resiliently deformable but relatively rigid and wherein said material assumes a predetermined functional form.

28. The septal defect occluder of claim 24 which includes an elongate flexible tether having a first end section and a second end section, said elongate tether extending from said first end section around said loop joinder links between said first and second plurality of arms to said second end section.

29. A septal defect occluder comprising:

a frame adapted to be inwardly radially collapsed from an expanded configuration to a collapsed configuration, said frame in the expanded configuration including a first plurality of spaced arms extending radially in a first plane, said first arms each having a base end, a second plurality of spaced arms extending radially in a second plane substantially parallel to and spaced from said first plane, said second arms each having a base end, and a plurality of spaced loop joinder links extending between the base ends of said first and second arms, the base end of each of said first arms being connected by said plurality of loop joinder links to base ends of two arms in said second plurality of arms, a first sheet of material supported by and extending over said first arms, and a second sheet of material supported by and extending over said second arms.

* * * * *